United States Patent [19]

Danos

[11] Patent Number: 4,821,304

[45] Date of Patent: Apr. 11, 1989

[54] DETECTION METHODS AND APPARATUS FOR NON-DESTRUCTIVE INSPECTION OF MATERIALS WITH RADIATION

[76] Inventor: Michael Danos, 4820 Hutchins Pl., Washington, D.C. 20007

[21] Appl. No.: 948,043

[22] Filed: Dec. 31, 1986

[51] Int. Cl.⁴ .............. G01N 23/201; G01N 23/203
[52] U.S. Cl. ................................ 378/86; 250/505.1
[58] Field of Search ............... 250/358.1, 505.1, 506, 250/507.1; 378/86, 87, 145, 146, 147, 156

[56] References Cited

U.S. PATENT DOCUMENTS

| | | | |
|---|---|---|---|
| 3,147,638 | 7/1965 | Sinclair | 378/86 |
| 3,243,589 | 3/1966 | Sinclair | 378/86 |
| 4,229,651 | 10/1980 | Danos | 378/147 |
| 4,437,006 | 3/1984 | Morgan et al. | 378/9 |
| 4,651,002 | 3/1987 | Anno | 250/358.1 |

OTHER PUBLICATIONS

Proposal for Development of the Slot Camera X-Ray Imaging System, Submitted by DMX Labs, 1983.
Yester, Barnes and King, Med. Phys. 8(2), Mar./Apr. 1981, p. 158.
Johns and Yaffe, Med. Phys. 9(2), Mar./Apr. 1982, p. 231.
Niklason, Sorenson and Nelson, Med. Phys. 8(5), Sep.-/Oct. 1981, p. 677.

*Primary Examiner*—Eugene R. LaRoche
*Assistant Examiner*—Nathan W. McCutcheon
*Attorney, Agent, or Firm*—Shlesinger & Myers

[57] ABSTRACT

Apparatus and methods for non-destructive radiation inspection including a radiation source, collimator, translatable slotted mask, adjustable resolution mask, and spaced scintillation counters is provided. Also provided is apparatus for one-sided inspection of materials which include an attenuation wedge, an X-ray tube alignment system and combination radiation direct detection on scatter detection arrays.

11 Claims, 4 Drawing Sheets

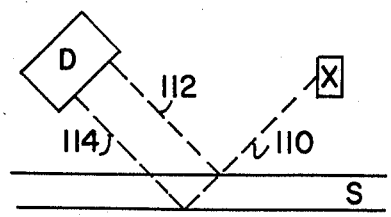
FIG. 9
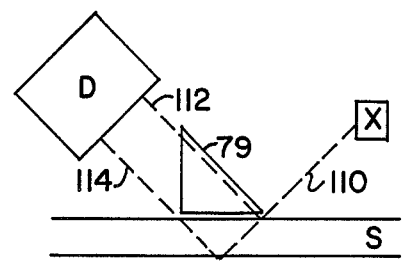
FIG. 10
FIG. 11
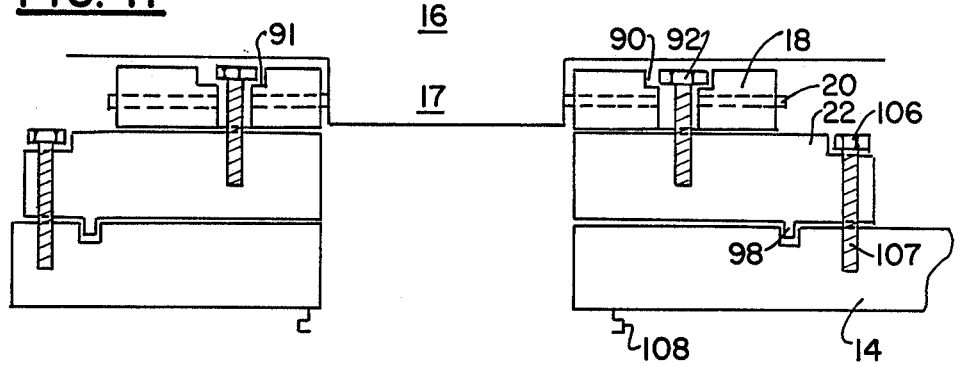
FIG. 12
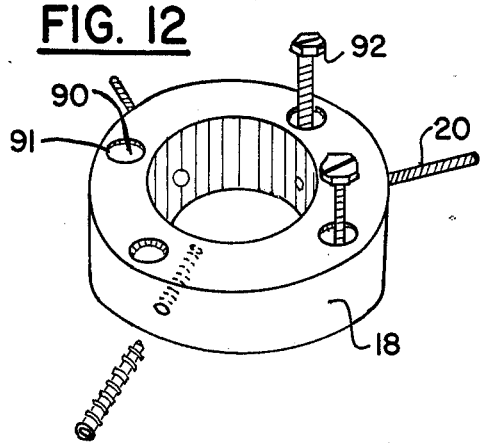
FIG. 13
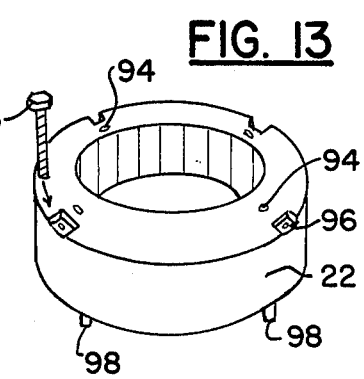
FIG. 14
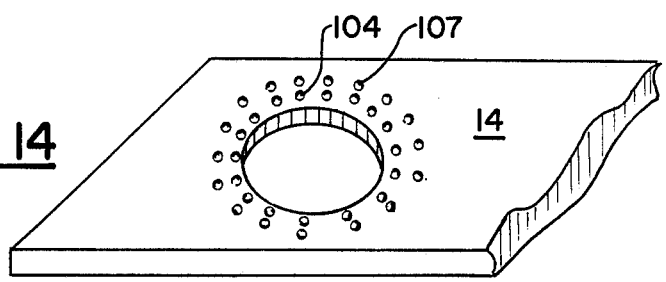

DETECTION METHODS AND APPARATUS FOR NON-DESTRUCTIVE INSPECTION OF MATERIALS WITH RADIATION

TECHNICAL BACKGROUND

This invention pertains to nondestructive radiation imaging and inspecting of articles employing scattered radiation and, more particularly, to methods and apparatus employing slot cameras to achieve high and low resolution inspection of such articles.

BACKGROUND OF THE INVENTION

The development of the subject matter described herein has evolved since the Inventor's initial work on a slot camera and method therefor described in U.S. Pat. No. 4,229,651 ('651). The earlier system basically provides a scattered radiation detection system by collimating and directing radiation (X-rays) from an appropriate source to a specimen wherein the radiation is scattered indiscriminately relatively uniformly in all directions from the specimen and detecting a defined portion of such scattered radiation. A brief recitation relating to the subject matter of that disclosure is now rendered in order to facilitate understanding of the developments leading to the instant invention.

In the '651 patent, the described slot camera, which is disposed perpendicularly to the radiation beam direction, is provided with a slotted mask to select primary scattered radiation from the specimen, i.e., that scattered directly from a particular point in the specimen, and direct to the detector camera that scattered radiation lying within a predetermined solid angle. Primary scattered radiation is distinguished from secondary radiation as it results from scattering of radiation originating from the source beam. Secondary scatter is caused by first scatter of primary radiation and, then, subsequent scattering of the scattered radiation in the sample. With the slot camera, the selection of the primary radiation is achieved by a combination of a slitted mask formed of radiation impervious material (generally lead) and baffles. The slit extends perpendicularly to the direction of the source beam, is aligned with the camera/detector, and preferably has a width approximately one-half that of the detector width in an approximate 1:1 general spatial relationship. Scattered radiation (photons) passing through the slit is subject to further selection by a series of "Buckey Baffles" composed of highly absorbent radiation material such as reinforced thin lead sheets. These baffles extend parallel to the direction of the collimated beam and lie in planes containing and extending radially outwardly from the source beam.

The baffles perform two functions. Because the baffles block entry of some of the potentially valid primary scatter radiation, their thickness should be not much more than 1/20 of the space between baffles. By this means, the baffles provide a predefined grid in the detected image without materially reducing image content. Also due to the radial alignment, the baffles serve to discriminate against secondarily scattered radiation. Therefore, substantially only primary scattered radiation is allowed to pass to the detector.

One of the benefits of the above-described slot camera concept is to minimize radiation intensity requirements by the efficient collection of primary scattered radiation within a well defined solid angle established by the slot, baffles and detector. Hence, some additional safety relating to beam intensity requirements is thereby introduced by the use of a slot camera.

Moving to an additional subject concerning the general state of the art, the detectors employed in the radiation field are now discussed. Most familiar are conventional films employed with direct imaging techniques. In addition to the fact that considerable radiation exposures are mandated in order to achieve an image, many structures will be masked or hidden behind more dense constituents stacked in the direction of alignment of the beam. Developments in the field have led to various scintillation and solid state counters, especially in X-ray detection technologies. To achieve more accurate detection, photomultipliers and discriminators arranged in an array of such counters are now becoming commonplace. Such detectors have the advantage of being capable of construction in a compact manner. Moreover, it is a simple matter to establish an array of such detectors where each individual detector is shielded with interstitial insulation from adjacent detectors by a radiation impervious material so as to eliminate cross-talk. Such a detector and detector array are described in related U.S. Pat. Nos. 4,437,006 and 4,284,895 to Morgan et al.

Where the above-described slot camera is employed, the detector detects substantially only primary radiation. The selection of primary radiation generates a band of scattered radiation corresponding to the scatter generated by a particular region in the specimen irradiated by the source beam. In essence, each band is comprised of a series of lines where each line represents scattering from a different incremental area within the irradiated region in the specimen. These bands are converted into an image via a computer program. As would be expected in this situation, either the specimen is moved or the detector is rotated about the specimen in a manner to image a series of different regions in order to provide a complete picture.

Turning now to another aspect of radiation scanning, it should be evident to one of ordinary skill in the art that the intensity of scattered radiation varies as a result of attenuation caused by some of the scattered radiation passing through a greater thickness of the specimen. In other words, as the collimated radiation passes into the sample, the intensity of scattering from points furthest from the detector (camera) would be less than from points closest to the detector due to the greater degree of absorption in the material. This phenomenon is referred to as "fall off" and is generally expressed as a logarithmic function ($e^{-x}$) where x is the distance travelled through the specimen. Of conventional techniques employed to compensate for fall off, one involves computation with computer programs designed to weight the intensity of the beam in a manner corresponding with the thickness of the sample.

Alternative corrective measures are described, for example, in applicant's '651 patent. For example, applying a second collimated radiation beam disposed 180° (opposite side) relative to the specimen will avoid exponential fall off because the use of the dual beam will alleviate the near side-far side attenuation difference. As with a single detector, the signals generated by the dual beam are conveyed to a memory buffer. However, unlike a single detector, it is required to use a computer to subtract the signals created by the scattering in the further sectors from the beam source. The signals are converted into a visual image, following subtraction and accounting for the fall off which in this case, follows a hyperbolic cosign function.

One purpose of the above-described slot camera/detector was its incorporation into conventional imaging systems, even direct transmission techniques such as computer assisted tomography (CAT) scanners. As is well known in the art of tomography, operation requires that the radiation source and detector be rotated about the specimen/subject to achieve a large number of exposures in the same plane but at different angles. When a series of exposures is completed, the source and detector are moved relative to the specimen to scan an immediately adjacent plane. The resulting picture is generated only after all the scans are completed, the appropriate detection/subtraction has been made and the signals compiled and then processed to provide the desired image. In view of the necessity to rotate the source and camera/detector through a multitude of circumferential positions relative to the specimen, it is evident that complex mechanical mounting and rotational drive assemblies are required. As a result, CAT scanners are large and complex pieces of equipment. Furthermore, since complete compilation and calculations are required, CAT provides a picture, not in real time but only after the appropriate computerized processing has been conducted.

Moving now to the problems recognized above and additional problems in the art, the following disadvantages are suffered in the known devices comprising the state of the art. Known devices are incapable of one side, non-destructive inspection of objects. Rotation about the specimen is necessary in order to achieve a complete picture or image. High intensity radiation is required in conventional direct transmission systems which suffer from the manifold disadvantage of requiring the specimen to be placed between the radiation source and the detector (film). Additionally, known detectors are virtually incapable of use for field application and inspection by means of scattering techniques of specimens such as turbine blades on a production line, aircraft wings, rocket segment joints, etc.

A host of ancillary, practical problems have also arisen concerning equipment, described above. For example, if a beam of a particular geometric cross-sectional configuration is desired, the entire collimator must be exchanged. Often such an exchange involves separation of the radiation source, generally a horizontally disposed X-ray tube, from the mounting assembly to exchange collimators or the tube, itself. As anyone practicing in this technical field can report, realignment of the X-ray tube with the associated detection mechanism is not a simple process. Furthermore, after such substitution, adjustments will be required not only between the tube and the mounting assembly but also between the collimator and the tube.

SUMMARY OF THE INVENTION

In view of the foregoing, it is an object of this invention to overcome limitations of the prior art.

It is another object of the invention to provide method and apparatus for detection of scattered radiation for on-line or laboratory inspection.

Another object of this invention is for fast inspection of high precision, mass produced articles.

It is another object of this invention to provide a one side X-ray imaging and inspection technique and apparatus.

Still another object of this invention is to provide an inspection system for real time analysis, cross-correlation and comparison where desired.

Yet another object of this invention is to supply method and apparatus for inspection of specimens requiring a minimum of mechanical manipulation of detection and radiation source apparatus.

Still another object of the invention is to provide method and apparatus which can be economically and conveniently combined with a plurality of known devices such as a combination of direct and scattered transmission inspection.

Still another object of this invention is to provide method and apparatus facilitating proper alignment of detectors with a beam of radiation emitted from a radiation source in equipment intended to be dismantled for transport between field locations.

These and other objects are satisfied by an apparatus for inspecting materials with a penetrating radiation emission means for emitting radiation capable of penetrating a material of predefined thickness, and collimator means for configuring said penetrating radiation into a beam of a selected cross-sectional geometry and directing said beam toward the material in a manner such that said beam penetrates a preselected volume of the material along a preselected cross-section thereof where said beam of radiation is scattered by the material. A portion of the scattered radiation is detected by a detector means for detecting said scattered radiation. In order to register the largest possible quantity of information provided by the slot camera arrangement, it is imperative to count the scattered X-ray photons rather than the X-ray photon flux which can be done, for example, by measuring the current generated in an X-ray detector. The X-ray photon counter preferably should conform to the geometry associated with the slot camera, i.e. it should be a strip of a width determined by the desired resolution and a length to cover the area as defined by the length of the slot in the "slitted mask". This detector could be of any suitable kind, for example, it could be a solid state counter, based, say, on silicon or germanium, etc., technology. In the following, the description will be given by using a scintillation counter as the example. The structure of such counters, involving scintillating material, light guides, and photomultipliers or some other light detector has by now become common place.

The scattered radiation to be detected is selected by means for selecting a desired portion of said scattered radiation and allowing said desired portion to impinge upon said detector means, said selection means comprising remotely spaced horizontal slitted mask means for permitting only a first portion of the scattered radiation to pass through perpendicular to the direction of the beam, and vertical means for permitting selection of a second portion of said first portion of radiation to pass through the detector means.

The slitted mask means is translatable to move in a plane between multiple positions and located between said specimen and said detector means and parallel to the direction of the beam, said slitted mask means being composed of radiation impervious material and having a slot (slit) for passing scattered radiation through said mask means in a manner where only said first radiation portion passes through the mask.

The first portion of radiation scattered from a region in the material is detected after being passed through said mask slit when in said first mask position. The mask is then moved to one or more other positions whereby scattered radiation from additional points may be detected after being passed through said mask. Without such movement, due to the nature of detectors described in the above-identified Morgan patents, periodic and regular blank spaces result in the overall picture from the interstitial insulation.

The foregoing objects and still others are satisfied by a variable resolution apparatus for inspection of materials by radiation comprising:

(a) radiation emission means for emitting a beam of radiation capable of penetrating a specimen and scattering from points therein, (b) adjustable collimator means for configuring the cross-sectional geometry of said beam and directing said beam at the specimen where the beam penetrates a preselected cylindrical volume of the specimen coaxial with the beam, (c) translatable slotted mask means for blocking portion of the radiation emitted from the specimen and allowing a portion of the emitted radiation to pass through the slot, said slotted mask means being translatable between at least a first and second position, and having adjusting means for changing the width of the slot, (d) resolution mask means for blocking a portion of the emitted radiation passing through said slotted mask means and allowing a portion of the emitted radiation to pass through, said resolution mask means being remotely spaced from said slotted mask means and movable between at least a first and second positions, said resolution mask means having alternating apertures and radiation blocking means where said apertures and blocking means are each of a preselected width, and having a preselected geometric configuration, detector means for detecting radiation passed through said resolution masking means, said detector means being positioned in close proximity to said resolution masking means including an array of detection elements and interstitial radiation insulators in a preselected geometric configuration, where said preselected geometric configuration substantially corresponds to the geometric configuration of said resolution mask means and alignable therewith, where moving said slotted mask means and said resolution mask relative to the detector permits adjustment of the resolution of detected radiation.

Further objects are satisfied by a radiation emission source alignment system comprising a mounting element, a seating means for receiving a portion of the source, said seating means having an aperture extending through its thickness for receiving the source window, positioning member having an aperture corresponding to said seating means aperture, said positioning member and said seating means being adapted to abut, position fixing means for fixing the position of said seating means and said positioning member relative to each other said fixing means being releasably and adjustably securable to said seating means and positioning member, connecting means for connecting said position fixing means to said mounting element, said connecting means having adjustable means for adjusting the position of said position fixing means relative to said connecting means in order to maintain the emission source in a horizontal position and an attachment member for removably attaching said connecting means to said position fixing means.

The above-stated objects are further satisfied by a method for adjustable resolution, one-sided radiation imaging, including the steps of:

(1) directing a beam of collimated radiation to a specimen which scatters a portion of the radiation, (2) selecting a first portion of the radiation by allowing it to pass through a first slot, (3) selecting a second portion of the first radiation portion within a predefined solid angle, (4) selecting a third portion of the second radiation portion to pass to a detector with an adjustable selecting means, (5) detecting the third portion of radiation where the third portion comprises radiation travelling along a precisely defined path.

BRIEF DESCRIPTION OF THE DRAWINGS

FIG. 9 is a schematic representation of scattering from one-sided inspection.

FIG. 10 is a schematic representation of scattering with an attenuation wedge.

FIG. 11 is a cutaway size view of the X-ray tube and the alignment assembly.

FIG. 12 is a perspective view of the tube attachment member.

FIG. 13 is a perspective view of the adjustable positioning member.

FIG. 14 is a perspective view of the mounting extension.

DETAILED DESCRIPTION OF THE ILLUSTRATED EMBODIMENT

Figure 1:
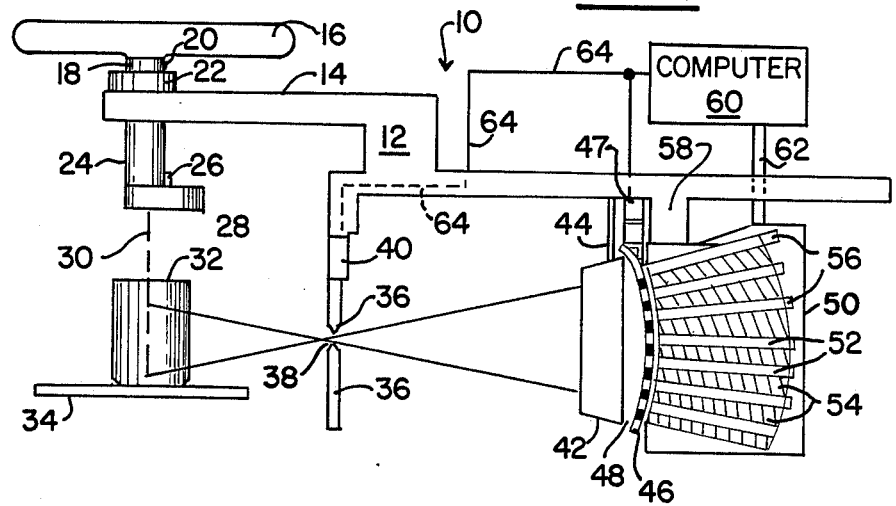
FIG. 1 is a schematic representation of a first detector system embodiment contemplated by this invention.

Referring to FIG. 1, radiation detector assembly 10 is illustrated in a dimensionally exaggerated manner. The assembly includes a frame 12 from which X-ray tube mounting extension 14 projects for supporting X-ray tube 16. X-ray tube 16 is attached to extension 14 by way of apertured attachment member 18 and apertured adjustable positioning member 22. Projecting radially into attachment member 18 are threaded alignment screws 20. A more detailed structural and functional recitation of the X-ray tube mounting arrangment is presented below.

Attached to the bottom side of mounting extension 14 is adjustable collimator 24 including rotating axial connecting member 26 to which rotatable collimator turret 28 is connected in a manner to permit rotation of turret 28 (much like a conventional microscope) about connecting member 26 thereby allowing selection of a particularly desired collimator. Preferably, the collimator is of the telescopic type which extends at least half the distance between tube 16 and specimen 32. A beam of X-rays generated from X-ray tube 16 passes through the apertured connection system into collimator 24 and is emitted, in this case, as a "pencil" beam directed to specimen 32, the target to be scanned. Specimen 32, like most articles, permits X-ray penetration. Also, like most articles as X-rays penetrate a portion, some of those X-rays are scattered. Thus, scatter is a function related to absorption of the X-rays by specimen 32. To assist in inspection of specimen 32, it is supported on specimen platform 34 to move it through detection system 10. Platform 34 is provided with conventional drive means for incremental movement (e.g., stepping motor and screw, not illustrated) to adjust the position of the specimen relative to detector assembly 10 and move specimen 32 incrementally.

Moving now to the detection portion of detection assembly 10, it includes slotted mask 36 composed of radiation impervious material such as lead. Slotted mask 36 features an intermediately disposed transverse slot of adjustable width. Although not illustrated in any detail, mask 36 can be constructed from two telescoping, interfitting sections where one is U-shaped. The two sections can be moved together or apart to widen or narrow slot 38. Such movement may be accomplished manually or by a motor. Slotted mask 36 is connected to translating motor 40 which in turn is connected to frame 12. Signals conveyed from a computer 60 over wires 64 causes translating motor 40 to move slotted mask 36 and, therefore, slot 38 in a direction parallel to the direction of pencil beam 30.

Remotely disposed from mask 36 are a series of baffles disposed in a radial configuration in planes containing pencil beam 30. Baffles 42 serve to discriminate and, therefore, avoid detection of secondarily scattered radiation from the specimen. Baffles 42 are connected to frame 12 by baffle mounting attachment 44. A general description of a slot camera presented thus far, excepting the translation of slot mask 36, is contained in U.S. Pat. No. 4,229,651 by the Inventor and, accordingly, the description is incorporated herein by reference.

An additional feature to the slot camera presented above is the resolution mask 46 (described more fully hereinbelow) including apertures (not illustrated) and lead strips 48. Resolution mask 46 is disposed behind baffles 42, conforms to the geometry of detector 50 facing mask 36 and is connected to translating motor 47 and to frame 12. Translating motor, actuated from signals conveyed from computer 60 through wires 64, is employed to move resolution mask 46 in a direction parallel to pencil beam 30.

Disposed immediately behind resolution mask 46 is detector 50 composed of a spaced array of scintillation counters 52 having interstitial insulating lead strips 54 disposed between each counter. It is preferable that counters 52 and strips 54 be arranged in an arc, the length of which corresponds to the maximum angular divergence of scattered radiation from specimen 32 passing through slot 38. The center of the arc, therefore, is defined by the center of slot 38. Counters 52 are of uniform size, thus strips 54 are wedge-shaped to provide the difference in thickness necessary to achieve the arc contour. Ideally, each counter measures between 2-4 millimeters wide, 20-40 centimeters in length and 5 centimeters deep. The long, narrow configuration of the exposed detection surface is provided to assist in selection of primary radiation. The Morgan patents, identified above, describe such detectors and for that reason are incorporated herein by reference. Hence, the stacked array of alternating detectors and interstitial radiation insulation is provided by this arrangement, except for the surface facing the radiation which herein is the length of the detector.

Figure 1A:
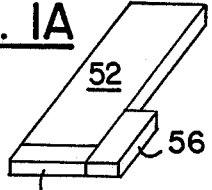
FIG. 1A illustrates the light collection arrangement employed.
Figure 16:
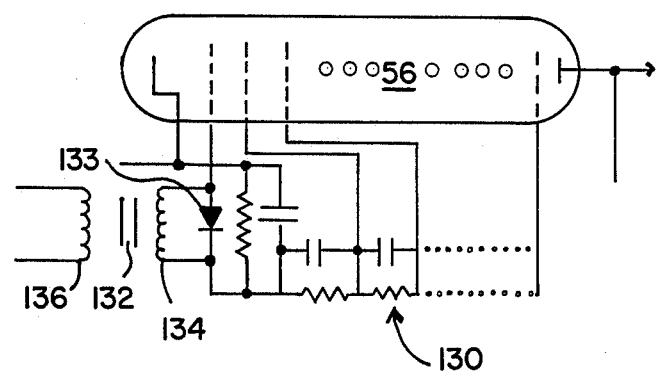
FIG. 16 is a circuit diagram of a photomultiplier dynode blocking switch.

Appropriately positioned and connected with scintillation counters 52 are photomultipliers 56 for converting received scintillation counts to electric pulses thereby facilitating more accurate and generally faster signal generation to the appropriate computer/processing apparatus. In order to collect the light from along the 20-40 cm length of the scintillator cell, a light pipe 51 lies along the edge of each counter (the 5 cm×2.4 mm edge) and directs the light from the counter to its associated photomultiplier 56. (See FIG. 1A). Photomultipliers 56 are electrically connected to the processor 60 through appropriate channels 62. It may prove advantageous to employ a slot camera in conjunction with a standard direct X-ray transmission system in which event the two systems would be employed alternatively or in alternation. In the latter case, fast switching circuitry would be employed in the slot camera detector arrangement 10 to switch the photomultiplier 56 on and off. Photomultiplier dynode blocking circuitry will provide such a switch. Turning briefly to FIG. 16, it depicts a photomultiplier 56 connected with circuit 130 having a pulse transformer 132 with isolation between primary coil 134 and secondary coil 136. When applying a pulse of desired polarity to the primary winding of the pulse transformer, the first dynode of the photomultiplier is driven negative and blocked. When the pulse is switched off, the diode 133 prevents the appearance of an opposite voltage pulse at the first dynode and permits it to return to its normal positive voltage.

Lastly, the entire curved detector array is mounted to frame 12 by mounting element 58 which may be of any conventional design.

As a final note concerning the apparatus in FIG. 1, it should be stressed that the geometries of the various described elements should be considered when developing a detector for particular purposes. For example, the distance between slot mask 36 and pencil beam 30, and between slot mask 36 and resolution mask 46, as well as the relative sizes of slot 38, strips 48, counters 52 and interstitial spacing 54 should be evaluated to achieve the intended inspection results (definition) desired.

Figure 2:
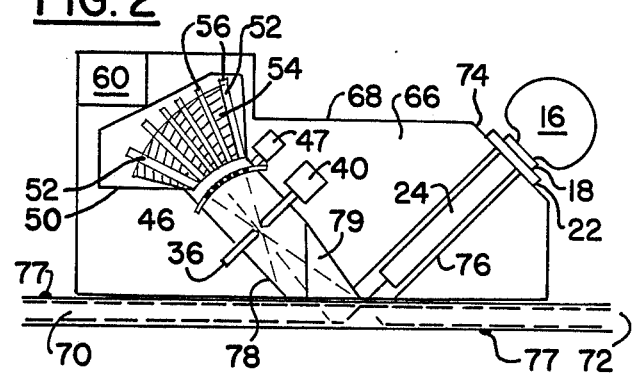
FIG. 2 is a schematic representation of a second detector system embodiment for physical one-sided inspection.

Given the above generalized description of one embodiment of the invention, Applicant now describes generally a second embodiment of the system before launching into a discussion concerning operation and detailed description of certain components identified in FIG. 1. FIG. 2 depicts an alternative radiation scanning device for one-sided inspection of a particular material. Scanning device 66 is encased in housing 68 constructed of appropriate materials which is adapted for placement on a structural member. For the purpose of this illustration, weld 72 between plates 70 (dashed lines) along a ship's hull is illustrated. The numbering of specific components contained in FIG. 2, which correspond to those in FIG. 1, are so identified.

Scanning device 66 includes X-ray tube source 16, mounting members 18 and 22, which attach to housing mounting element 74. Collimator 24 is attached to housing 66 to provide a pencil beam of radiation to weld 72.

The X-rays scatter from weld 72 into oppositely disposed conduit 78. Conduit 78 is preferably lined with lead or some other radiation impervious material and is disposed at an angle of approximately 45° to plate 70 and substantially perpendicular to conduit 76. Attenuation wedge 79 is located at the opening of conduit 78. Attenuation wedge 79 is positioned to interfere with the passage of a portion of the collimated radiation travelling through the conduit. Its purpose is to compensate for the relative difference in intensity of scattered radiation from the portion of weld 72 closest to the detector and that furthest away from the detector. Hence, the wedge serves to provide somewhat uniform intensity of scattered radiation generated by weld 72.

Briefly, wedge 79 is composed of tin, copper, aluminum or like material and may be incorporated as part of the device, as illustrated, or may be a stand-alone unit and achieve the same results. Accounting for the particular application, use of a wedge will result in generation of uniform scintillation counts across the entire depth of the specimen for like scattering and avoid the need to adjust the gain to compensate for the location of the scatter, unless desired. Its function is more fully described below in the discussion relating to FIGS. 9 and 10. Also located within conduit 78 are translatable slotted mask 36 connected to translating motor 40 and resolution mask 46 connected to translation motor 47. Positioned behind resolution mask 46 is detector 50. Also, illustrated are locator beads 77, a series of which can be placed at any location along weld 72. Locator beads are composed of lead or some other X-ray absorbing material and serve to assist the operator in pinpointing the location of the pencil beam relative to weld 72. As is easily observed from FIG. 2, the apparatus provided by this invention, is capable not only of one-sided inspection and detection of scattered radiation from a selected specimen but also physical disposition of the assembly on only one side of the specimen.

Figure 3:
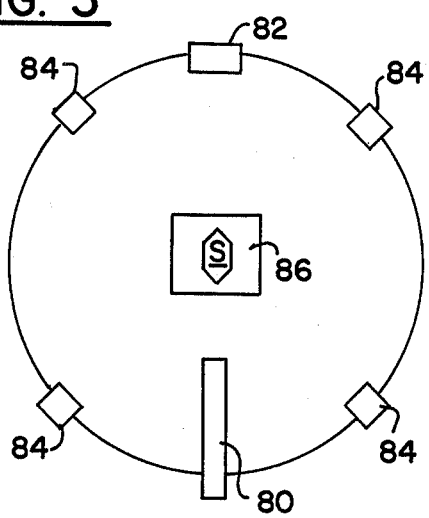
FIG. 3 is a diagramatic representation of a combination of direct and scattered radiation detection system according to this invention.

A final alternative arrangement for use of the inspection system, described above, is that illustrated schematically in FIG. 3. In FIG. 3 is illustrated a combination inspection system incorporating one-sided scattering detection concepts and direct transmission detection. One distinction between this embodiment and those described above is that this embodiment is incapable of one-sided inspection due to incorporation of the direct detecting elements. In this case, collimated X-ray beam source is aligned directly opposite direct radiation detector 82 which can be of any conventional variety. Specimen S is disposed at the bisector of the line defined by X-ray source 80 and direct detector 82. Disposed at 45°, 135°, 225° and 315° relative to beam source 80, is an array of four slot detectors 50 (described above) for detecting radiation scattered from specimen S. It is preferred that the array of slot detectors 84, direct detector 82, and beam source 86 be aligned in a plane. It is possible to move this entire configuration relative to the sample but if possible, due to the nature of the specimen, the specimen may be moved through planar array in a direction perpendicular to that plane, or it could be rotated around its axis, and it also could be translated along its axis, such motion being that of a screw. Accordingly, specimen S can be placed on platform 86 which allows its movement in the desired manner with respect to the array of detectors. In this combination system, alignment apparatus described below becomes a critical economic factor by allowing a tube or collimator to be substituted with a minimum of realignment effort.

In a system of this type imaging is not contemplated. The signals produced are cross-correlated with these of a known perfect specimen; the signals from which are stored in a computer and read out in real time for comparison with these produced by a specimen under test.

The structural and functional relationships between slotted mask 36, resolution mask 46 and detector 50 are now described. As noted above, the geometries of the precise arrangement are governed by the particular application. However, for purposes of illustration equidistance spacing between specimen 32 and mask 36 and then between mask 36 and detector 50 will be assumed. Also, the width of slot 38 will be assumed and the width of slot 38 will be assumed to be one-half the width of counter 52. Strips 48 of resolution mask 46 will have a width equal to slot 38 and apertures 49 will equal the length of counter 52.

Figure 4:
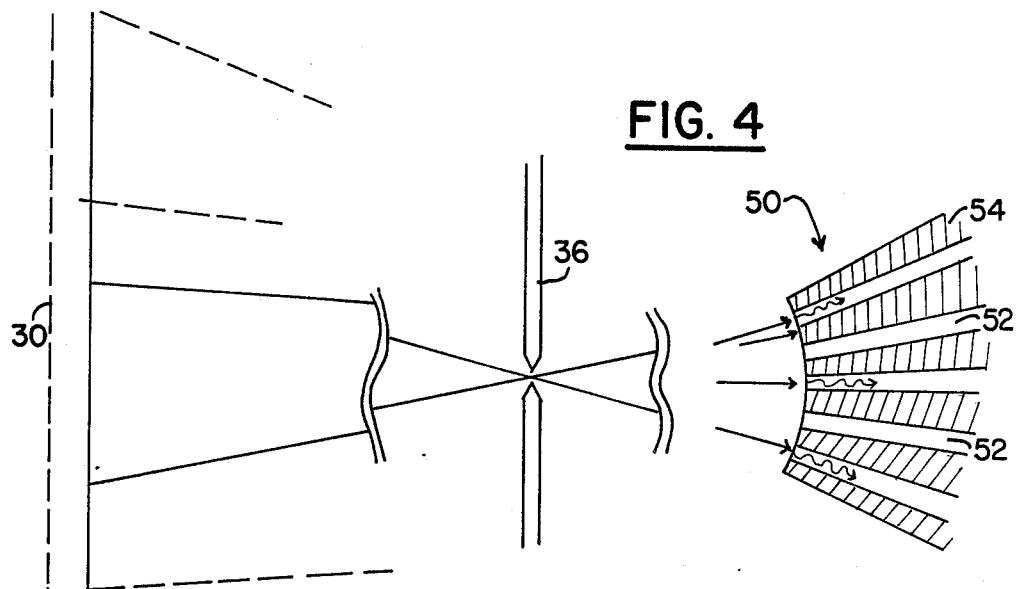
FIG. 4 is an exaggerated schematic illustrating detection of scattered radiation.

FIG. 4 schematically represents how slotted mask 36 selects X-rays scattered from primary beam 30, only from a selected portion of sample S. Those X-rays which are counted by detector array 50 must impinge directly on counters 52. Others which impinge on interstitial insulation 54 are not counted. Accordingly, it is necessary to move slotted mask 36 in order to detect those regions which produced primary scattered X-rays impinging on the interstitial spacers.

Figure 5:
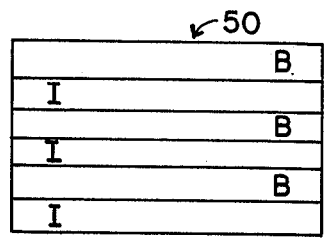
FIG. 5 is a representation of an image picture resulting from one scatter exposure.

Turning now to FIG. 5, it schematically represents an image obtained from detector array 50 from one exposure of scattered radiation from pencil beam 30. The alternating sectors represent imaged (I) and dead space of blank (B). Dead space B is caused by interstitial insulations 54 in the detector array. The width of image sectors I and blank sectors B are equivalent in FIG. 5, thereby indicating that the width of interstitial insulators 54 and counters 52 are equal.

In order to eliminate the horizontal shadows of image display illustrated in FIG. 5, slotted mask 36 is translated in a direction perpendicular to the direction of elongation of the illustrated bands. Such translation permits detection of scattered radiation from region in the specimen previously undetected due to impingement of the primary scattered radiation on insulation 54. Hence, with the assistance of appropriate processing, a total image of the specimen cross-section will be obtained upon two exposures.

Figure 6:
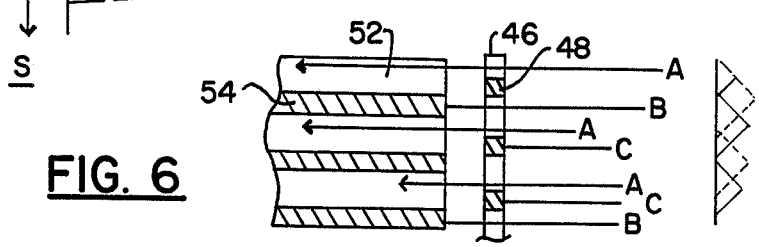
FIG. 6 is a representation of partial blocking by the resolution mask.
Figure 7:
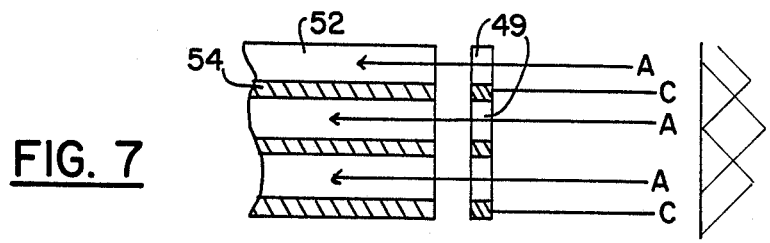
FIG. 7 represents the resolution mask in the neutral position.
Figure 8:
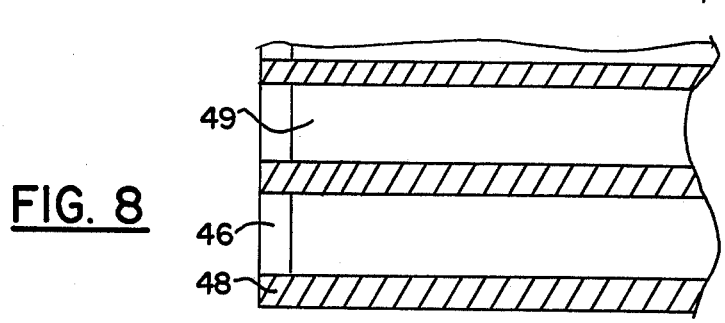
FIG. 8 is a partial front view of the resolution mask.

The function of resolution mask 46 and its effect on detector 50 is illustrated in FIGS. 6, 7 and 8. Before discussing those figures, the general elementary geometric concept underlying mask 46 is briefly recited. Considering one counter 52 and its corresponding region of specimen 32, it should be evident that the highest number of counts (peak) will occur at the central portion of the specific region corresponding to the center of counter 52. Moving away from the center causes a decrease in counts (intensity). This decrease continues to the edges of counter 52 where the counts decrease to zero. Thus, the count intensity is represented by a triangle with the peak corresponding to the center and the bottom of the legs corresponding to the counter edges. The size of the triangle and degree of overlap of triangles determined by adjacent counters can be manipulated by moving the resolution mask relative to the counters. It is such manipulation which provides for readily adjustable resolving capabilities of this invention.

In FIG. 8, a corner of resolution mask 46 is illustrated. Although not clearly illustrated in this representation, it should be understood that the configuration of resolution mask 46 should be substantially identical to the associated detector. For example, if detector 50 presents a curved face, then mask 46 should be curved. Mask 46 is composed of plexiglass or some other appropriate material. Mask 46 has apertures 49, which correspond to the surface dimensions of counters 52. Disposed between each of apertures 49 are lead strips 48. In FIG. 8, apertures 49 have a height approximately twice that of lead strips 48. The edges of mask 46 is seated in a track (not illustrated) along which it is translated. Where low resolution is desired, apertures 49 are aligned with counters 52 and strips 48 are in the neutral position (aligned with insulation 54). Assuming proper geometric configuration and eliminating consideration of the dead space caused by insulation 54, the resolution "triangles" formed by each counter overlap to the extent that the bottom of the legs directly underlie the peak from the adjacent counter (see FIG. 7). If, however, it is desired to obtain "high" resolution of the region of specimen 32, strips 48 are moved to block a portion of counter 52. As roughly illustrated in FIG. 6, no overlap occurs in the resolution triangles (solid lines). Because of the intensity differences, after a comparatively longer exposure time sufficient to obtain adequate counts to establish the triangles, slotted mask 36 is moved in order to obtain an additional exposure of the portions of the selected specimen region not originally scanned (dashed lines). The sum of the corresponding counts (the height of the triangles) is substantially uniform across the entire scan. Hence, the image produced is of equal intensity.

FIG. 7 depicts the function of resolution strips 48. Lead strips 48 are aligned with insulation 54 in a manner where transmission of scattered X-rays A pass through to counters 52 and X-rays C are blocked by lead strips 48. Since lead strips 48 overlie interstitial insulation 54, no blockage by resolution mask 46 occurs. Resolution is increased by translating mask 46 to a position depicted in FIG. 6. Here, lead strips 48 have been moved to block approximately half the width of counters 52. Strips 48 no longer overlie insulation 54. Accordingly, some of X-rays A are still detected by counters 52, X-rays C are blocked by lead strips 48 and X-rays B are blocked by interstitial insulation 54. As a result of this arrangement, approximately half the X-ray imaging intensity is obtained in FIG. 6 compared with FIG. 7. Therefore, due to moving resolution mask 46 into a blocking mode (as illustrated in FIG. 6), it is necessary to increase exposure time of the detector in order to achieve sufficient counts to generate an appropriate image. It should be evident that when the additional geometric factor of insulation 54 is introduced to obtain a complete image, it is necessary to translate slitted mask 36 and resolution mask 46 into different positions relative to one another and detector 50 in order to achieve total imaging of the specimen.

An alternative arrangement for resolution mask 46 is to provide a louvered linkage for adjustment of the width of strips 48 relative to detector 50. If pivotally mounted, much in the fashion of a venetian blind, it provides not only "high" and "low" resolution measurements but also intermediate settings. Such linkages are well known.

Figure 15:
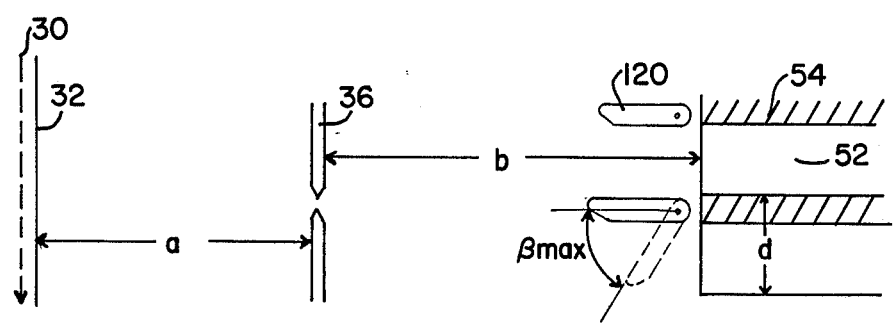
FIG. 15 is a schematic representation of a pivoting baffle type resolution mask.

Another form of resolution mask 46 is schematically illustrated in FIG. 15. In this arrangement, mask 46 actually is comprised of a series of pivotable baffles 120 having a curved, knife-shaped cross-section to accommodate passage of proper radiation. Like the louvered arrangement, this type of system provides for a spectrum of different resolving capabilities by precise positioning relative to counters 52. Where the operator desires enhanced resolution, the number of exposure positions required is expressable by N=d/r where d is the counter spacing and r is smallest desired effection aperture. The travel distance of slotted mask can be expressed as $$D = \frac{a+b}{a} \times d \times \left(\frac{N-1}{N}\right)$$

where a equals the distance between the pencil beam and the slotted mask, b equals the distance between the slotted mask and the counter, N equals the number of exposure positions, and d equals the counter spacing. Finally the step size required for movement of baffles 120 is $$\Delta = D/N$$

By moving baffle 120 to the position for highest resolution, thus requiring the longest exposure period due to the smallest count rate and the largest number of incremental steps N, the rotation angle equals $\beta$ max. Values of lesser rotation up to $\beta=0°$ are achievable for intermediate and lowest resolution settings.

Referring now to FIGS. 9 and 10, the function of attenuation wedge 79 is more fully described. In FIG. 9 is illustrated a schematic representation of scanning specimen S with radiation emitted from source X. For the purpose of illustration, it will be assumed that radiation travels along a pencil beam designated line 110 to and into specimen S. Radiation oriented toward detector D is scattered from the upper surface and lower surface along lines 112 and 114, respectively. It is evident that radiation following the path defined by lines 110 and 114 must pass through a far greater amount of the specimen than radiation travelling along path defined by lines 110 and 112. Radiation travelling along lines 110 and 112 would suffer from little secondary scatter and attenuation in contrast to that travelling along lines 110 and 114. Hence, the intensity of primary scatter X-rays travelling path 112 would be greater than that travelling along path 114 and it becomes necessary for the operator to adjust the gain of detector D to focus either on the closer or furthest specimen regions.

Turning to FIG. 10, the same arrangement is illustrated but now with attenuation wedge 79. Radiation travelling along the path defined by line 114 passes from specimen S without any interference from wedge 79. However, radiation passing along the path defined by line 112 passes through wedge 79 in a manner to interfere with the passage of a portion of that radiation and, ideally, create an equal degree of attenuation as is experienced by the X-rays following path 110 and 114. The geometry of wedge 79 and the material used in its composition will depend largely on the source beam energy, the degree of X-ray attenuation of the specimen and the geometries employed in detection. Determination of the best arrangement is well within the scope of routineer practices of the skilled artisan.

The alignment system described with reference to FIGS. 11-14 are now described.

Focusing now on specific details relating to the alignment system briefly mentioned above, it comprises attachment member 18, positioning member 22 and mounting extension 14. Conventional tubes include a projecting circumferential port 17 from which X-rays are emitted. The instant invention contemplates an arrangement employing an X-ray tube attachment member containing an aperture corresponding substantially to the cross-sectional geometry of port 17 and into which port 17 is seated.

Attachment member 18 is positioned to surround port 17 where port 17 projects into the aperture provide by member 18. Threaded, radially converging alignment screws 20 are tightened about port 17 so as to fix the relative position of tube 16 to positioning member 18. Disposed at regular intervals around the upper surface of member 18 are bore holes 90 projecting through the entire thickness of member 18. Bore holes 90 include a recessed shelf 91. Bores 90 are adapted to loosely receive threaded bolts 92 but have a smaller diameter than the head of bolt 92 where the head can lodge against shelf 91. Hence, where properly configured, bolt 92 is recessable within bore 90 on shelf 91.

Member 18 is adapted to be positioned on positioning member 22. Bored through the top surface of positioning member 22 are precision tapped holes 94 which correspond to the outer diameter of bolt 92. Member 18 and member 22 are attached to each other by passing bolt 92 through bore 90 and screwing the bolt into bore threaded holes 94. Before tightening bolts 92, the relative position of members 18 and 22 to each other is adjusted by sliding member 18 relative to member 22 until the desired position for maximum emission of X-rays from port 17 is achieved. Once the proper relative position is determined, bolts 92 are tightened whereby frictional engagement between the head of bolt 92 and shelf 91 prevents sliding movement between members 18 and 22.

Due to the individual characteristics exhibited by individual X-ray tubes, no one, fixed, standardized spacing and alignment mechanism is possible to achieve maximum transmission. The positional adjustability of members 22 and 18 allows for a permanent means for securing an individual X-ray tube to an appropriate mounting frame without the need for total realignment when a tube is substituted. Once aligned, mounting of the X-ray tube having members 18 and 22 attached thereto is achieved by securing mounting member 18 to an appropriate mounting frame extension designated herein as 14. Since it is desirable to maintain the X-ray tube in a horizontal position and use of the instant invention may require movement of the entire frame which would move X-ray tube 16 from a horizontal position, adjustable positioning member 22 is provided with precision positioning pins 98 projecting from the bottom surface thereof and adapted to correspond to and be received by a mounting member in precision positioning apertures 104.

As observed in FIG. 14, mounting member 14 includes a series of regularly spaced, precision positioning apertures 104, circumferentially disposed about the large port aperture. When the desired alignment of tube 16 to member 14 is established, pins 98 are pushed into apertures 104 and threaded bolts 106 are screwed through corresponding threaded bores 96 in member 22 and into the precision threaded bores 107 in extension 14. Accordingly, X-ray tube 16 is attachable in a precision manner to mounting extension 14.

One additional provision featured generally in the foregoing alignment mechanism is the inclusion of collinator mounting bracket 108 disposed on the opposite surface of extension 14 from apertures 104 and bores 107. The purpose of bracket 108 is to facilitate substitution, replacement or removal of collimator 24.

As briefly noted above, the benefits of the described mounting and alignment system is most evident in practice as a labor saving device. Since every X-ray tube has its own signature, every time a new X-ray tube is placed on a detection apparatus or the tube is moved in order to maintain the horizontal position, it is necessary for the operator to realign the tube with the apparatus. Proper angles and alignment of port 17 must be achieved to obtain maximum transmission efficiencies. The alignment system disposes with the need to adjust the position of bore 17 relative to frame 14 for each change.

When the combination system depicted in FIG. 3 is employed, the alignment system provides fine adjustments without which alignment would consume considerable labor. In the combination system, great care is required to align the source, the direct transmission detector and each slot camera of the array. One technique involves mounting dental X-ray film in front of each of the slot camera detectors where each includes a lead wire crosshair. A triangular slot mask is disposed between the specimen and the film which provides a triangular shaped scatter pattern. The specimen is irradiated and film developed. When the intersecting crosshairs appear centrally disposed within the triangle, the camera is properly aligned. If not centrally disposed, the relative position source and/or slot cameras/direct detector may be finely adjusted to maximize transmission efficiencies.

Many variations and modifications of the abovedescribed embodiments are within the ordinary skill of the skilled artisan in this art, without departing from the scope of the invention. Accordingly, those modifications and embodiments are intended to fall within the scope of the invention as defined by the following claims:

I claim:

1. An apparatus for inspecting materials, comprising:
    a penetrating radiation emission means for emitting radiation capable of penetrating a material of predefined thickness,
    collimator means for configuring said penetrating radiation into a beam of a selected cross-sectional geometry and directing said beam toward the material in a manner where said beam penetrates a preselected volume of the material along a preselected cross-section thereof where said beam radiation is scattered by the material,
    detector means for detecting said scattered radiation,
    scattered radiation selection means for selecting a desired portion of said scattered radiation and allowing said desired portion to impinge upon said detector means, said selection means comprising remotely spaced vertical mask means with a horizontal slitted means for permitting only a first portion of the scattered radiation to pass through perpendicular to the direction of the beam, and vertical resolution mask means for permitting selection of a second portion of said first portion of radiation to pass through to the detector means, and
    said slitted mask means being translatable to move between a first and second and third position and located between said specimen and said detector means and perpendicular to said detector means, said slitted mask means being composed of radiation impervious material and having a slot for passing scattered radiation through said mask means in a manner where only said first radiation portion passes through the mask.

2. An apparatus according to claim 1 where said slitted mask means includes adjustment means for adjusting the width of the slit.

3. A variable resolution apparatus for inspection of materials by radiation comprising:
  (a) radiation emission means for emitting a beam of radiation capable of penetrating a specimen and scattering from points therein,
  (b) adjustable collimator means for configuring the cross-sectional geometry of said beam and directing said beam at the specimen where the beam penetrates a preselected cross-sectional area of the specimen,
  (c) translatable slotted mask means for blocking a portion of the radiation emitted from the specimen and allowing a portion of the emitted radiation to pass through the slot, said slotted mask means being translatable between at least a first and second position, and having adjusting means for changing the width of the slot,
  (d) resolution mask means for blocking a portion of the emitted radiation passing through said slotted mask means and allowing a portion of the emitted radiation to pass through, said resolution mask means being remotely spaced from said slotted mask means and movable between at least a first and second positions, said resolution mask means providing alternating apertures and radiation blocking means where said apertures and blocking means have a preselected geometric configuration,
  detector means for detecting radiation passed through said resolution masking means, said detector means being positioned in close proximity to said resolution masking means including an array of detection elements and interstitial radiation insulation in a preselected geometric configuration, where said preselected geometric configuration substantially corresponds to the geometric configuration of said first position of said resolution mask means and alignable therewith,
  where moving said slotted mask means and said resolution mask relative to the detector permits adjustment of the resolution of detected radiation.

4. An apparatus according to claim 3 where said radiation beam is scattered from the specimen and said slotted mask means is positioned at an angle of between 45° and 135° to the direction of said beam.

5. An apparatus according to claim 4 where said detector is comprised of an array of elongated scintillation or solid state counters coupled with photomultipliers or preamplifiers having strips of lead shielding disposed between each counter and the ratio of the thickness of said strip shielding and said counters is an integer number, and said resolution mask is a plexiglass or other material sheet having elongated apertures sized to correspond to the surface dimensions of said counters and said blocking means are dimensioned to correspond with said strip shielding where said resolution mask is translated perpendicular to the direction of elongation of said apertures.

6. An apparatus according to claim 5 where said slotted mask means is translated between a first position to allow impingement of radiation from a first specific region in the specimen on a first counter and a second position to allow impingement of radiation from a second specific region adjacent to said first region and where said blocking means of said resolution means is positioned adjacent to said strip shielding, and third.

7. An apparatus according to claim 3 where said detector includes an array of scintillation or solid state counters and interstitial insulation and a resolution mask including a series of pivotal blocking members capable of movement between a position fully blocking said counters and fully exposing said counters.

8. An apparatus according to claim 3 where said detection elements are scintillation counters and further comprising photomultipliers for amplifying a signal from said counters where said photomultipliers include a dynode circuit means for fast activation and deactivation of said photomultiplier.

9. An apparatus according to claim 8 further comprising an attenuation wedge.

10. In combination,
  a direct radiation detector,
  a penetrating radiation emission means for emitting radiation capable of penetrating a material of predefined thickness,
  collimator means for configuring said penetrating radiation into a beam of a selected cross-sectional geometry and directing said beam toward the material in a manner where said beam penetrates a preselected volume of the material along a preselected cross-section thereof where a portion of said beam radiation is scattered by the material,
  an array of detection means disposed in a plane with said emission means and said direct detector for detecting said scattered radiation said detector means including a solid state counter means or a scintillation means for scintillating upon impingement of scattered radiation thereon and means for counting the number of scintillations,
  scattered radiation selection means for selecting a desired portion of said scattered radiation and allowing said desired portion to impinge upon said detector means, said selection means comprising remotely spaced vertical mask means with a horizontal slitted means for permitting only a first portion of the scattered radiation to pass through perpendicular to the direction of the beam, and vertical resolution mask means for permitting selection of a second portion of said first portion of radiation to pass through the detector means,
  said slitted mask means being translatable to move between a first and second position and located between said specimen and said detector means and perpendicular to said detector means, said slitted mask means being composed of radiation impervious material and having a slot for passing scattered radiation through said mask means in a manner where only said first radiation portion passes through the mask.

11. A method for adjustable resolution, one-sided radiation imaging, including the steps of:
  (1) directing a beam of collimated radiation to a specimen which scatters a portion of the radiation,
  (2) selecting a first portion of the radiation by allowing it to pass through a first slot,
  (3) selecting a second portion of the first radiation portion within a predefined solid angle,
  (4) selecting a third portion of the second radiation portion to pass to a detector with an adjustable selecting means,
  (5) detecting the third portion of radiation where the third portion comprises radiation travelling along a precisely defined path.

* * * * *